(12) United States Patent
Shaw (10) Patent No.: US 8,048,143 B2
(45) Date of Patent: Nov. 1, 2011

(54) MEDICAL DEVICES

(75) Inventor: William J. Shaw, Cambridge, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 540 days.

(21) Appl. No.: 12/139,033

(22) Filed: Jun. 13, 2008

(65) Prior Publication Data

US 2008/0312731 A1 Dec. 18, 2008

Related U.S. Application Data

(62) Division of application No. 10/762,816, filed on Jan. 22, 2004, now Pat. No. 7,854,756.

(51) Int. Cl.
*A61F 2/06* (2006.01)
(52) U.S. Cl. ...................................... 623/1.15
(58) Field of Classification Search .............. 623/1.15, 623/1.38–1.54, 23.7–23.76, 23.64, 23.65, 623/23.66, 23.69; 606/139, 144, 148, 151–157, 606/191–201
See application file for complete search history.

(56) References Cited

U.S. PATENT DOCUMENTS

| | | | |
|---|---|---|---|
| 4,001,172 A * | 1/1977 | Steinkamp et al. | 524/504 |
| 4,446,579 A | 5/1984 | Inamori et al. | |
| 4,655,771 A | 4/1987 | Wallsten | |
| 4,832,895 A * | 5/1989 | Johnson | 264/29.1 |
| 4,888,311 A * | 12/1989 | Davidovits et al. | 501/95.2 |
| 4,922,905 A | 5/1990 | Strecker | |
| H812 H * | 8/1990 | George | 524/444 |
| 4,946,919 A * | 8/1990 | Johnson | 526/285 |
| 5,015,253 A | 5/1991 | MacGregor | |
| 5,169,397 A * | 12/1992 | Sakashita et al. | 606/27 |
| 5,195,969 A | 3/1993 | Wang et al. | |
| 5,219,959 A * | 6/1993 | Inoue et al. | 525/537 |
| 5,238,742 A * | 8/1993 | Freeman et al. | 428/367 |
| 5,270,086 A | 12/1993 | Hamlin | |
| 5,366,504 A | 11/1994 | Andersen et al. | |
| 5,380,298 A | 1/1995 | Zabetakis et al. | |
| 5,468,544 A | 11/1995 | Marcolongo et al. | |
| 5,470,345 A | 11/1995 | Hassler et al. | |
| 5,509,931 A | 4/1996 | Schmitt | |
| 5,514,112 A | 5/1996 | Chu et al. | |
| 5,527,353 A | 6/1996 | Schmitt | |
| 5,556,426 A | 9/1996 | Popadiuk et al. | |
| 5,593,719 A | 1/1997 | Dearnaley et al. | |
| 5,629,077 A | 5/1997 | Turnlund et al. | |
| 5,637,641 A * | 6/1997 | Becker et al. | 525/102 |
| 5,645,934 A | 7/1997 | Marcolongo et al. | |
| 5,674,242 A | 10/1997 | Phan et al. | |
| 5,679,470 A | 10/1997 | Mayer | |

(Continued)

FOREIGN PATENT DOCUMENTS

DE 19 730 296 1/1999

(Continued)

OTHER PUBLICATIONS

U.S. Appl. No. 10/263,225, filed Oct. 2, 2002, Bertolino et al.

(Continued)

*Primary Examiner* — Alvin J. Stewart
(74) *Attorney, Agent, or Firm* — Fish & Richardson P.C.

(57) ABSTRACT

Medical devices including one or more ceramic fibers are disclosed. In some embodiments, each dimension of the ceramic fiber(s) is equal to or greater than one micron.

17 Claims, 6 Drawing Sheets

U.S. PATENT DOCUMENTS

| | | | | |
|---|---|---|---|---|
| 5,690,670 | A | 11/1997 | Davidson | |
| 5,705,122 | A * | 1/1998 | Curran | 264/625 |
| 5,709,703 | A | 1/1998 | Lukic et al. | |
| 5,709,713 | A | 1/1998 | Evans et al. | |
| 5,718,973 | A | 2/1998 | Lewis et al. | |
| 5,725,570 | A | 3/1998 | Heath | |
| 5,725,573 | A | 3/1998 | Dearnaley et al. | |
| 5,733,326 | A | 3/1998 | Tomonto et al. | |
| 5,767,218 | A * | 6/1998 | Becker et al. | 528/25 |
| 5,780,807 | A | 7/1998 | Saunders | |
| 5,797,877 | A | 8/1998 | Hamilton et al. | |
| 5,800,511 | A | 9/1998 | Mayer | |
| 5,800,519 | A | 9/1998 | Sandock | |
| 5,849,415 | A * | 12/1998 | Shalaby et al. | 428/419 |
| 5,899,935 | A | 5/1999 | Ding | |
| 5,928,260 | A | 7/1999 | Chin et al. | |
| 5,962,007 | A * | 10/1999 | Cooper et al. | 424/426 |
| 5,964,745 | A * | 10/1999 | Lyles et al. | 604/891.1 |
| 5,980,972 | A | 11/1999 | Ding | |
| 5,984,905 | A | 11/1999 | Dearnaley | |
| 5,989,376 | A * | 11/1999 | Kusy et al. | 156/166 |
| 6,015,432 | A | 1/2000 | Rakos et al. | |
| 6,054,532 | A | 4/2000 | Wang et al. | |
| 6,066,100 | A | 5/2000 | Willard et al. | |
| 6,087,025 | A | 7/2000 | Dearnaley et al. | |
| 6,099,561 | A | 8/2000 | Alt | |
| 6,147,135 | A * | 11/2000 | Yuan et al. | 523/105 |
| 6,161,399 | A | 12/2000 | Jayaraman | |
| 6,162,244 | A | 12/2000 | Braun et al. | |
| 6,165,178 | A | 12/2000 | Bashiri et al. | |
| 6,165,213 | A | 12/2000 | Goicoechea et al. | |
| 6,190,373 | B1 | 2/2001 | Palermo et al. | |
| 6,248,129 | B1 | 6/2001 | Froix | |
| 6,248,571 | B1 | 6/2001 | Schmidt et al. | |
| 6,250,952 | B1 | 6/2001 | Shiga et al. | |
| 6,264,689 | B1 | 7/2001 | Colgan et al. | |
| 6,280,457 | B1 | 8/2001 | Wallace et al. | |
| 6,303,697 | B1 * | 10/2001 | Yuan et al. | 525/240 |
| 6,312,458 | B1 | 11/2001 | Golds | |
| 6,316,018 | B1 | 11/2001 | Ding et al. | |
| 6,331,184 | B1 | 12/2001 | Abrams | |
| 6,335,029 | B1 | 1/2002 | Kamath et al. | |
| 6,340,360 | B1 * | 1/2002 | Lyles et al. | 604/890.1 |
| 6,340,441 | B1 | 1/2002 | Meyer et al. | |
| 6,425,898 | B1 | 7/2002 | Wilson et al. | |
| 6,428,571 | B1 | 8/2002 | Lentz et al. | |
| 6,451,059 | B1 * | 9/2002 | Janas et al. | 623/23.51 |
| 6,468,266 | B1 | 10/2002 | Bashiri et al. | |
| 6,468,304 | B1 | 10/2002 | Dubois-Rande et al. | |
| 6,488,694 | B1 | 12/2002 | Lau et al. | |
| 6,506,408 | B1 | 1/2003 | Palasis | |
| 6,520,952 | B1 | 2/2003 | Jimenez | |
| 6,524,345 | B1 * | 2/2003 | Valimaa et al. | 623/23.56 |
| 6,551,352 | B2 | 4/2003 | Clerc et al. | |
| 6,558,794 | B1 | 5/2003 | Fehrenbacher et al. | |
| 6,573,331 | B1 | 6/2003 | Camberlin et al. | |
| 6,589,286 | B1 | 7/2003 | Litner | |
| 6,676,987 | B2 | 1/2004 | Zhong et al. | |
| 6,692,499 | B2 | 2/2004 | Tormala et al. | |
| 6,733,533 | B1 | 5/2004 | Lozier | |
| 6,762,025 | B2 * | 7/2004 | Cubicciotti | 435/6 |
| 6,805,706 | B2 | 10/2004 | Solovay et al. | |
| 6,807,440 | B2 | 10/2004 | Weber | |
| 6,955,716 | B2 * | 10/2005 | Xu et al. | 106/35 |
| 7,029,495 | B2 | 4/2006 | Stinson | |
| 7,037,304 | B2 * | 5/2006 | Lyles et al. | 604/891.1 |
| 7,037,562 | B2 * | 5/2006 | Jimenez | 428/36.4 |
| 7,083,641 | B2 | 8/2006 | Stinson | |
| 7,160,929 | B1 * | 1/2007 | Tan | 521/73 |
| 7,232,429 | B2 | 6/2007 | Moreci | |
| 7,244,497 | B2 * | 7/2007 | Hartmann et al. | 428/373 |
| 7,250,381 | B2 * | 7/2007 | Jaffee | 442/162 |
| 7,294,406 | B2 | 11/2007 | Canham et al. | |
| 7,419,633 | B1 * | 9/2008 | Jimenez | 264/573 |
| 7,462,366 | B2 | 12/2008 | Lanphere | |
| 7,491,225 | B2 * | 2/2009 | Weber et al. | 623/1.11 |
| 7,494,950 | B2 | 2/2009 | Armitage et al. | |
| 7,517,353 | B2 * | 4/2009 | Weber | 606/200 |
| 7,625,337 | B2 * | 12/2009 | Campbell et al. | 600/156 |
| 7,713,955 | B2 * | 5/2010 | Whiteford et al. | 514/183 |
| 7,803,457 | B2 * | 9/2010 | Irwin et al. | 428/323 |
| 7,854,756 | B2 * | 12/2010 | Shaw | 623/1.15 |
| 2002/0016596 | A1 | 2/2002 | Cooper | |
| 2002/0165523 | A1 | 11/2002 | Chin et al. | |
| 2003/0018380 | A1 | 1/2003 | Craig et al. | |
| 2003/0065355 | A1 | 4/2003 | Weber | |
| 2003/0093107 | A1 | 5/2003 | Parsonage et al. | |
| 2003/0125804 | A1 * | 7/2003 | Kruse et al. | 623/2.1 |
| 2003/0143350 | A1 * | 7/2003 | Jimenez | 428/35.2 |
| 2003/0176849 | A1 | 9/2003 | Wendlandt et al. | |
| 2004/0052861 | A1 * | 3/2004 | Hatcher et al. | 424/602 |
| 2005/0149102 | A1 * | 7/2005 | Radisch et al. | 606/194 |
| 2005/0163954 | A1 * | 7/2005 | Shaw | 428/36.1 |
| 2005/0261721 | A1 * | 11/2005 | Radisch et al. | 606/192 |
| 2006/0015136 | A1 * | 1/2006 | Besselink | 606/200 |
| 2006/0079624 | A1 * | 4/2006 | Nava et al. | 524/492 |
| 2006/0184237 | A1 * | 8/2006 | Weber et al. | 623/1.44 |
| 2006/0204556 | A1 * | 9/2006 | Daniels et al. | 424/443 |
| 2006/0208231 | A1 * | 9/2006 | Shalaby | 252/500 |
| 2006/0282156 | A1 * | 12/2006 | Weber et al. | 623/1.19 |
| 2007/0117911 | A1 * | 5/2007 | Irwin et al. | 524/495 |
| 2007/0144124 | A1 * | 6/2007 | Schewe et al. | 55/487 |
| 2007/0190880 | A1 * | 8/2007 | Dubrow et al. | 442/181 |
| 2007/0202342 | A1 * | 8/2007 | Whiteford et al. | 428/425.5 |
| 2007/0255392 | A1 * | 11/2007 | Johnson | 623/1.15 |
| 2008/0021212 | A1 * | 1/2008 | Whiteford et al. | 540/472 |
| 2008/0034801 | A1 * | 2/2008 | Canham et al. | 65/439 |
| 2008/0051881 | A1 * | 2/2008 | Feng et al. | 623/1.39 |
| 2008/0077222 | A1 * | 3/2008 | Johnson et al. | 623/1.2 |
| 2008/0103444 | A1 * | 5/2008 | Jimenez | 604/103.09 |
| 2008/0207581 | A1 * | 8/2008 | Whiteford et al. | 514/183 |
| 2008/0312731 | A1 * | 12/2008 | Shaw | 623/1.13 |
| 2009/0182088 | A9 * | 7/2009 | Irwin et al. | 524/495 |
| 2009/0198219 | A1 * | 8/2009 | Campbell et al. | 604/524 |
| 2009/0227944 | A1 * | 9/2009 | Weber | 604/96.01 |
| 2010/0007240 | A1 * | 1/2010 | Kornbluh et al. | 310/309 |
| 2010/0055336 | A1 * | 3/2010 | Patel et al. | 427/391 |
| 2010/0173070 | A1 * | 7/2010 | Niu | 427/215 |
| 2010/0203529 | A1 * | 8/2010 | Kuslich et al. | 435/6 |
| 2010/0211158 | A1 * | 8/2010 | Haverty et al. | 623/1.15 |
| 2010/0318108 | A1 * | 12/2010 | Datta et al. | 606/151 |

FOREIGN PATENT DOCUMENTS

| | | |
|---|---|---|
| EP | 0 923 913 | 6/1999 |
| WO | WO 96/12448 | 5/1996 |
| WO | WO 96/17634 | 6/1996 |
| WO | WO 99/32051 | 7/1999 |
| WO | WO 99/61081 | 12/1999 |
| WO | WO 00/38590 | 7/2000 |
| WO | WO 01/34062 | 5/2001 |
| WO | WO 03/015840 | 2/2003 |
| WO | WO 03/055534 | 7/2003 |
| WO | WO 03/082565 | 10/2003 |

OTHER PUBLICATIONS

U.S. Appl. No. 10/688,224, filed Oct. 15, 2003, Tan.
U.S. Appl. No. 60/331,332, filed Sep. 28, 2001, Parsonage et al.
U.S. Appl. No. 60/327,629, filed Oct. 5, 2001, Horn et al.
U.S. Appl. No. 10/849,742, filed May 20, 2004, Chen et al.
Harper, C.A., "Handbook of Plastics and Elastomers", 1975, 4 pages.
Lorca, J.L., "Fatigue of particle- and whisker-reinforced metal-matrix composites", *Progress in Materials Science* 47 (2002) 283-353.

* cited by examiner

MEDICAL DEVICES

CROSS REFERENCE TO RELATED APPLICATIONS

This application is a divisional application under 35 U.S.C. §120 of U.S. application Ser. No. 10/762,816, filed on Jan. 22, 2004 now U.S. Pat. No. 7,854,756, the entire contents of which are hereby incorporated by reference.

TECHNICAL FIELD

The invention relates to medical devices, such as, for example, stents, stent-grafts, and grafts, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

To support a passageway open, endoprostheses are sometimes made of relatively strong materials, such as stainless steel or Nitinol (a nickel-titanium alloy), formed into struts or wires.

SUMMARY

The invention relates to medical devices.

In one aspect, the invention features a medical device having a structure that includes a first ceramic fiber. Each dimension of the fiber is equal to or greater than one micron.

In another aspect, the invention features a medical device having a structure that includes a ceramic fiber and a non-ceramic fiber. The ceramic fiber is intertwined with the non-ceramic fiber.

In a further aspect, the invention features a method of making a medical device. The method includes co-knitting a ceramic fiber with a non-ceramic fiber. Each dimension of the ceramic fiber is equal to or greater than one micron.

In another aspect, the invention features a medical device with a structure including a mixture. The mixture includes a polymer and ceramic fibers. Each dimension of the fibers is equal to or greater than one micron.

In a further aspect, the invention features a medical device with a structure that has a first layer including a polymer and a second layer including a ceramic fiber.

In another aspect, the invention features a medical device that includes a tubular structure and a polymer element on the tubular structure. The polymer element includes a ceramic fiber. Each dimension of the ceramic fiber is equal to or greater than one micron.

In a further aspect, the invention features a medical device (e.g., a stent, a graft, a stent-graft, a medical balloon, a catheter) that includes a ceramic fiber, each dimension of the fiber being equal to or greater than one micron.

Embodiments may also include one or more of the following.

The first ceramic fiber can include a first metalloid (e.g., silicon or boron) and a second metalloid. The first ceramic fiber can include silicon borocarbonitride.

The first ceramic fiber can include a metalloid (e.g., silicon) and a non-metallic element. The first ceramic fiber can include silicon nitride and/or silicon carbide.

The first ceramic fiber can include a metallic element (e.g., aluminum, calcium) and a nonmetallic element. The first ceramic fiber can include aluminum oxide and/or calcium oxide.

The ceramic fiber (e.g., the first ceramic fiber) can be at least about five microns long. The ceramic fiber (e.g., the first ceramic fiber) can be from about five microns to about 25,000 microns long (e.g., from about ten microns to about 1,000 microns long, from about ten microns to about 100 microns long).

The ceramic fiber (e.g., the first ceramic fiber) can be at least about five microns wide (e.g., from about five microns to about 500 microns wide, about ten microns wide). The ceramic fiber (e.g., the first ceramic fiber) can be from about one micron to about 50 microns wide.

The ceramic fiber can have an aspect ratio of from about 5:1 to about 500:1 (e.g., from about 5:1 to about 200:1).

The first ceramic fiber can extend continuously along an entire length of the device.

The first ceramic fiber can extend helically about the device.

The device can further include a second ceramic fiber that is different from the first ceramic fiber. The first and second ceramic fibers can be co-knitted or co-woven.

The device can be formed substantially of one or more ceramic fibers and/or can be reinforced by one or more ceramic fibers.

The device can further include a non-ceramic fiber.

The structure can be a tubular member.

The device can be in the form of a stent (e.g., a drainage stent), a graft, a stent-graft, a medical balloon, or a catheter.

The device can further include a polymer layer that is carried by the structure.

The device can further include a therapeutic agent. The ceramic fiber can include a therapeutic agent. The first layer can include a therapeutic agent.

Each dimension of the ceramic fiber can be equal to or greater than one micron.

The non-ceramic fiber can include stainless steel and/or a nickel-titanium alloy.

The ceramic fiber can be knitted, woven, twisted (e.g., intertwined), tied, or braided. The ceramic fiber can be knitted, woven, twisted (e.g., intertwined), tied, or braided with the non-ceramic fiber.

The ceramic fibers can be at least about five microns long. The ceramic fibers can be from about five microns to about 25,000 microns long.

Embodiments of the invention can include one or more of the following advantages. Ceramics are relatively inert, e.g., they resist oxidation or scaling. As a result, they are relatively biocompatible. Ceramics can have reduced occurrences of chemical, mineral, and/or bacterial deposits or encrustations. Low encrustation can be advantageous for certain medical devices, such as, for example, kidney drainage stents. Some ceramics are porous and can be used as drug carriers. Ceramics are durable (e.g., they can withstand frictional forces with relatively little wear), and are strong and flexible. Thus, ceramics are advantageous for use in certain medical devices, such as grafts. Ceramics also are advantageous for use in certain medical devices because ceramics are MRI-compatible.

The details of one or more embodiments of the invention are set forth in the accompanying drawings and the description below. Other aspects, features, and advantages of the invention will be apparent from the description and drawings, and from the claims.

DETAILED DESCRIPTION

Figure 1:
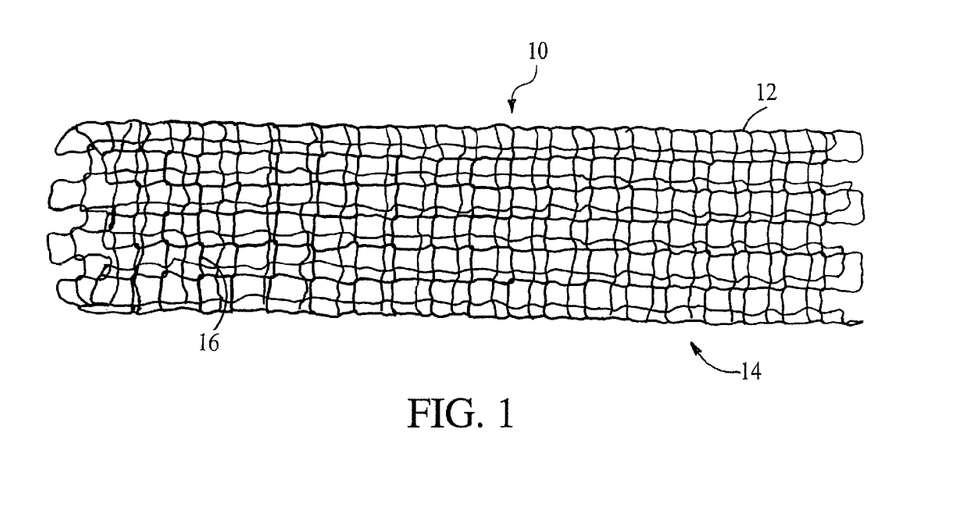
FIG. 1 is a perspective view of an embodiment of an endoprosthesis.

Referring to FIG. 1, an endoprosthesis 10 (as shown, a stent) includes a ceramic fiber 12 formed into a deformable tubular member 14. Endoprosthesis 10 is capable of being deformed from a first, compacted shape to a second, expanded shape in which it can support a vessel in the body. As shown, fiber 12 is knitted to form a series of interlocked loops 16 such that the fiber extends continuously along the length of tubular member. Fiber 12 generally includes a ceramic material that is non-corrosive and experiences relatively low encrustation, e.g., microbial growth. Additionally, the ceramic material can be resistant to wear resulting from frictional forces, e.g., when used in an abdominal aortic aneurysm (AAA) stent-graft that is exposed to high shearing forces. Thus, ceramic fiber 12 is relatively biocompatible, durable, and good for medical use.

Ceramic fiber 12 generally includes an inorganic material having non-metallic properties. For example, ceramic fiber 12 can include a metallic element and a non-metallic element, a metalloid and a non-metallic element, or two metalloids. As used herein, "metalloid" means those elements exhibiting chemical characteristics that are between metallic and non-metallic characteristics. Metalloids include boron, silicon, germanium, arsenic, antimony, tellurium and polonium. "Metallic elements" include those in Groups 3-12 of the period table. "Non-metallic elements" include those elements, such as carbon, nitrogen, and oxygen, generally located on the periodic table to the right of the metalloids.

Ceramic fiber 12 can be commercially available. For example, silicon borocarbonitride, which is both an example of a ceramic having a metalloid (Si) and a non-metallic element (N), and an example of a ceramic having two metalloids (B and Si), is commercially available from Bayer Aktiengesellschaft (Leverkusen, Germany), as SIBORAMIC. Examples of ceramics having a metallic element and a non-metallic element include aluminum oxide fibers with added yttrium oxide and zirconium oxide, available from 3M (Minnesota) as Nextel™ Fibers.

In some embodiments, fiber 12 can have a width or diameter of from about five microns to about 1000 microns. Fiber 12 can have a width or diameter that is equal to or greater than about five microns (e.g., greater than about 100 microns, greater than about 200 microns, greater than about 300 microns, greater than about 400 microns, greater than about 500 microns, greater than about 600 microns, greater than about 700 microns, greater than about 800 microns, greater than about 900 microns), and/or equal to or less than about 1000 microns (e.g., less than about 900 microns, less than about 800 microns, less than about 700 microns, less than about 600 microns, less than about 500 microns, less than about 400 microns, less than about 300 microns, less than about 200 microns, less than about 100 microns).

In certain embodiments (e.g., when fiber 12 is used in a woven or knitted graft or covering), fiber 12 has a width or diameter of from about five microns to about 20 microns (e.g., about ten microns), or a width or diameter of from about 100 microns to about 1000 microns (e.g., about 500 microns). In some embodiments (e.g., when fiber 12 is used to form a knitted, co-knitted or woven stent), fiber 12 has a width or diameter of from about ten microns to about 500 microns (e.g., about 50 microns).

Fiber 12 can have a cross-section that is circular or non-circular, such as oval, or regularly or irregularly polygonal having three, four, five, six, seven, or eight or more sides. In some cases, fiber 12 can be flat. Fiber 12 can be in the shape of a ribbon (e.g., a flat or wavy ribbon). Along its length, fiber 12 can be, for example, straight, wavy, coiled, or folded.

After ceramic fiber 12 is provided, the fiber can be formed into endoprosthesis 10 according to known processes. For example, fiber 12 can be knitted on a circular knitting machine as described, for example, in Heath, U.S. Pat. No. 5,725,570, and Andersen, U.S. Pat. No. 5,366,504. Ceramic fiber 12 can be woven, as described in Mayer, U.S. Pat. No. 5,800,511, or crocheted. In other embodiments, endoprosthesis 10 can be formed by tying or knotting ceramic fiber 12, as described in Sandock, U.S. Pat. No. 5,800,519. In still other embodiments, ceramic fiber 12 can be used to form endoprosthesis 10 according to Wallsten, U.S. Pat. No. 4,655,771. In some cases, ceramic fiber 12 can be twisted, bent, or coiled to form endoprosthesis 10.

In general, endoprosthesis 10 can be of any desired shape and size (e.g., coronary stents, aortic stents, peripheral stents, gastrointestinal stents, urology stents, drainage stents, anastomosis stents, and neurology stents). Depending on the application, endoprosthesis 10 can have a diameter of, for example, from one millimeter to 46 millimeters. In certain embodiments, a coronary stent can have an expanded diameter of from about two millimeters to about six millimeters. In some embodiments, a peripheral stent can have an expanded diameter of from about five millimeters to about 24 millimeters. In certain embodiments, a gastrointestinal and/or urology stent can have an expanded diameter of from about six millimeters to about 30 millimeters. In some embodiments, a neurology stent can have an expanded diameter of from about one millimeter to about 12 millimeters. An abdominal aortic aneurysm (AAA) stent and a thoracic aortic aneurysm (TAA) stent can have a diameter of from about 20 millimeters to about 46 millimeters. A drainage stent, e.g., suitable for use in a urethra or a ureter, can have a diameter of from about two millimeters to about ten millimeters. An anastomosis stent can have a diameter of from about two millimeters to about 50 millimeters.

After endoprosthesis 10 is formed, it can be used, e.g., delivered and expanded, according to conventional methods. Methods of stent delivery include, but are not limited to, balloon expansion, self expansion, or a combination of balloon expansion and self expansion. Delivery methods are described, for example, in Strecker, U.S. Pat. No. 4,922,905; Andersen et al., U.S. Pat. No. 5,366,504; Lukic et al., U.S. Pat. No. 5,709,703; and Lau et al., U.S. Pat. No. 6,488,694. Self-expansion can be used to expand relatively non-elastic materials by, for example, the incorporation of elastic structures within the design of the device. As an example, an endoprosthesis can be formed of an elastic fiber that is co-knit with a ceramic fiber. As another example, an endoprosthesis can be formed of a mixture of elastic material and relatively non-elastic material. Suitable catheter systems are described in, for example, Wang, U.S. Pat. No. 5,195,969, and Hamlin, U.S. Pat. No. 5,270,086. Suitable stents and stent delivery are also exemplified by the Radius® or Symbiot® systems, available from Boston Scientific Scimed, Maple Grove, Minn.

Numerous other embodiments including ceramic fibers 12 are possible.

For example, endoprosthesis 10 can be modified into a stent-graft. The components of the stent-graft (e.g., the stent or the graft) can include ceramic fibers, polymers, metals, or combinations thereof. The components can include the same materials or different materials. For example, the stent alone can include ceramic fibers, the graft alone can include ceramic fibers, or both the stent and the graft can include ceramic fibers. The stent can be metal, while the graft includes ceramic fibers. In some cases, the stent-graft can include and/or can be attached to a biocompatible, non-porous or semi-porous polymer matrix made of, for example, polytetrafluoroethylene (PTFE), expanded PTFE, polyethylene, urethane, or polypropylene.

Figure 2A:
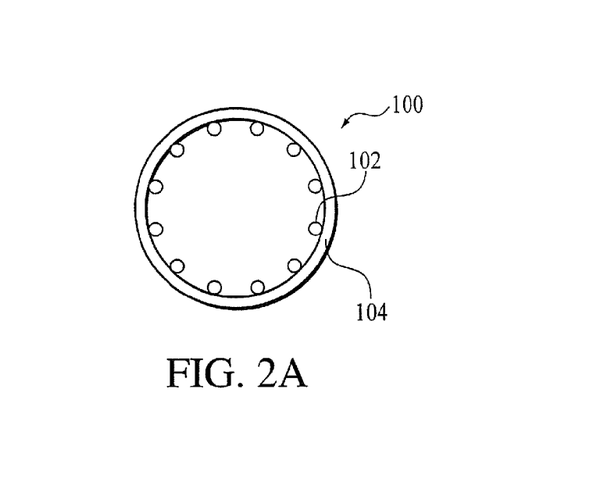
FIG. 2A is an end view of an endoprosthesis.
Figure 2B:
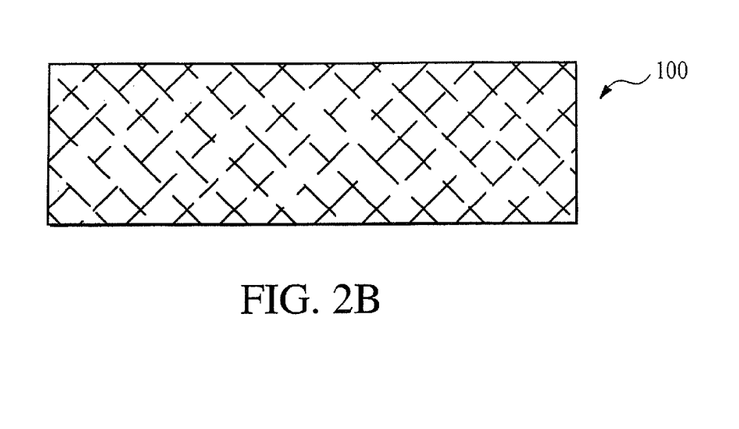
FIG. 2B is a side view of the endoprosthesis of FIG. 2A.
Figure 2C:
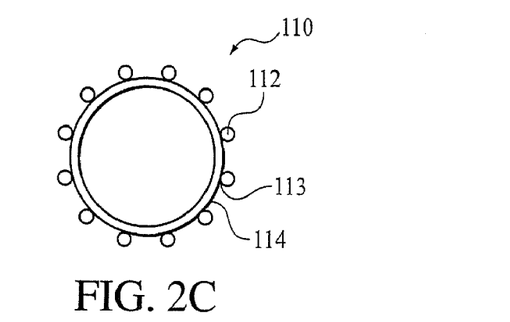
FIG. 2C is an end view of an endoprosthesis.
Figure 2D:
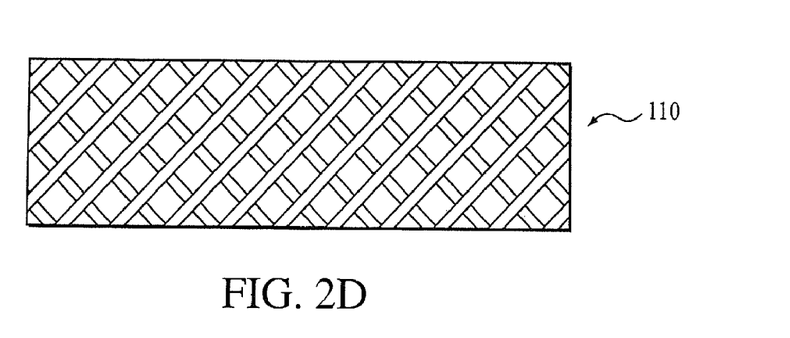
FIG. 2D is a side view of the endoprosthesis of FIG. 2C.
Figure 2E:
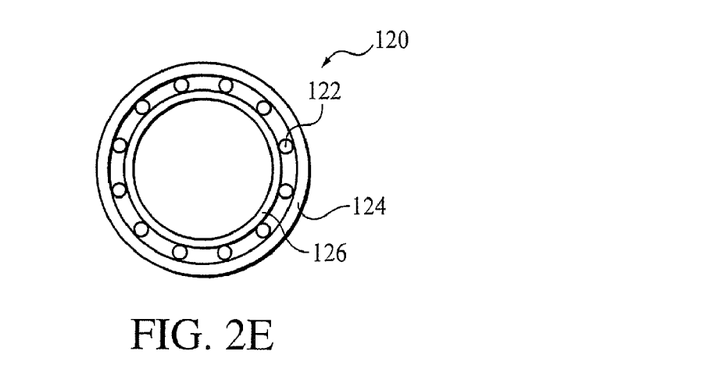
FIG. 2E is an end view of an endoprosthesis.
Figure 2F:
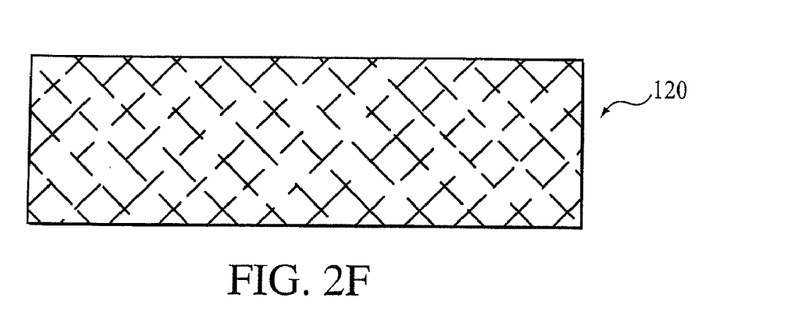
FIG. 2F is a side view of the endoprosthesis of FIG. 2E.

Referring now to FIGS. 2A-2F, the stent-graft can have any of a number of different forms. For example, and referring specifically to FIGS. 2A and 2B, a stent-graft 100 includes a stent 102 covered by a graft 104. Advantages to such a structure can include enhanced protection of the stent during delivery. In FIGS. 2C and 2D, a stent-graft 110 includes a stent 112 that is lined on its interior surface 113 by a graft 114. Graft 114 can provide stent 112 with enhanced strength and/or can decrease the amount of turbulence in blood flow through stent 112. In some cases, and referring now to FIGS. 2E and 2F, a stent-graft 120 includes a stent 122 that is both covered by a graft 124 and lined by a graft 126.

Figure 3A:
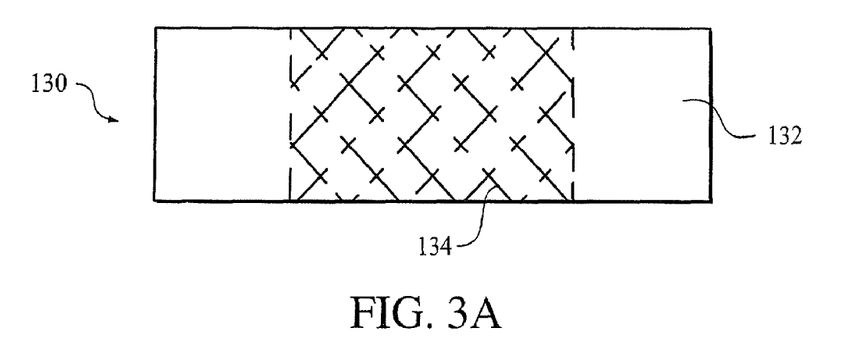
FIG. 3A is a side view of an endoprosthesis.
Figure 3B:
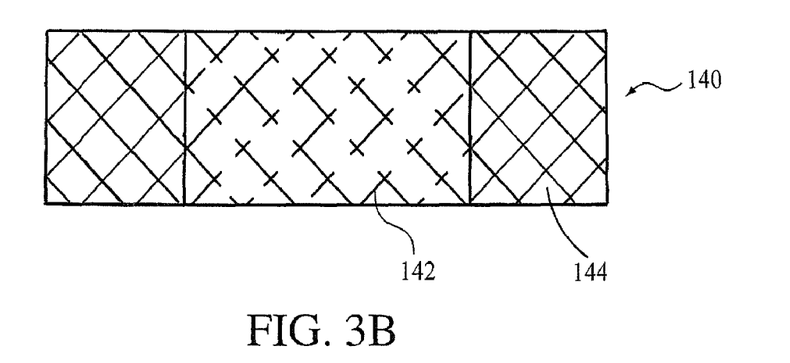
FIG. 3B is a side view of an endoprosthesis.
Figure 3C:
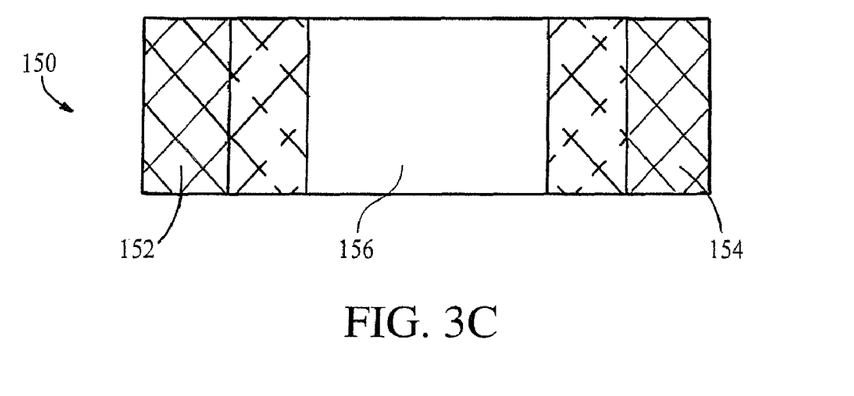
FIG. 3C is a side view of an endoprosthesis.

The graft and the stent in the stent-graft can have the same length or different lengths. For example, in FIG. 3A, a stent-graft 130 includes a stent 134 and a graft 132 that is longer than the stent. In FIG. 3B, on the other hand, a stent-graft 140 includes a stent 144 and a graft 142 that is shorter than the stent. In some cases, the stent-graft can include more than one stent. As an example, and referring now to FIG. 3C, a stent-graft 150 includes two stents, 152 and 154, that are connected, and partially covered, by a graft 156. In some embodiments, at least one of the stents is entirely covered by the graft.

Figure 4A:
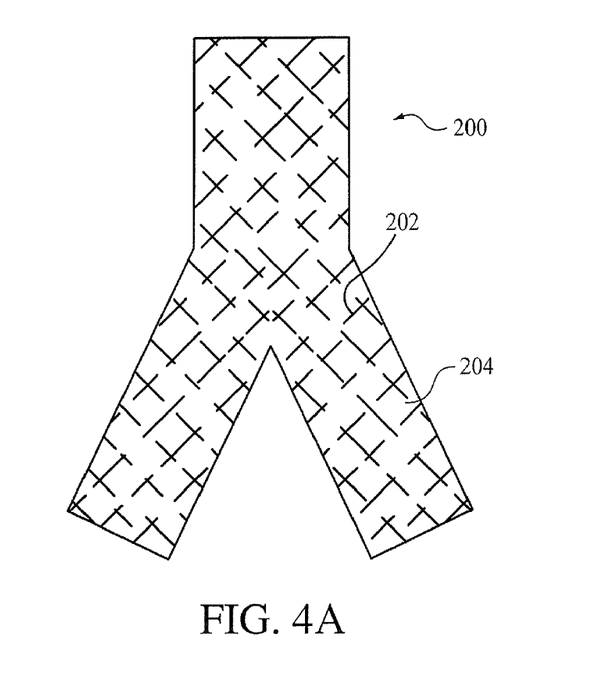
FIG. 4A is a side view of an endoprosthesis.
Figure 4B:
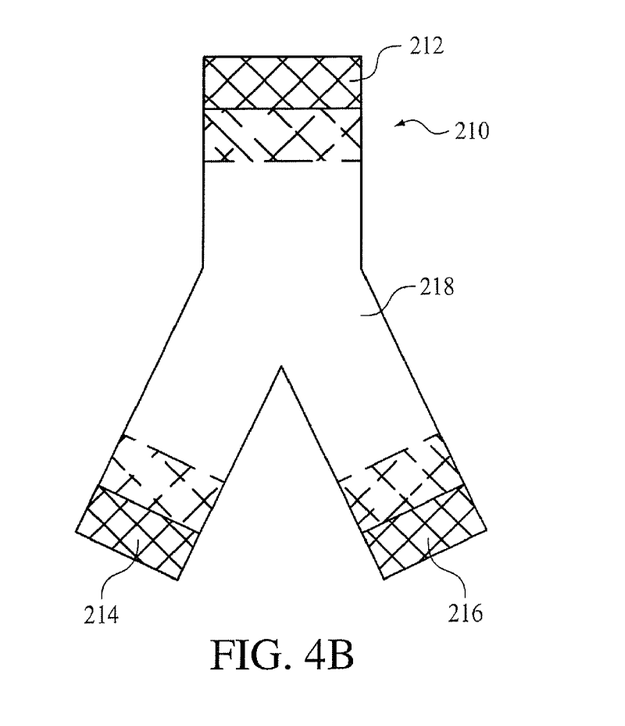
FIG. 4B is a side view of an endoprosthesis.

Referring now to FIGS. 4A and 4B, the stent-graft can be bifurcated. For example, the stent-graft can be an abdominal aortic aneurysm (AAA) stent-graft. In FIG. 4A, an AAA stent-graft 200 includes a stent 202 that is entirely covered by a graft 204. In some embodiments, stent 202 can be a single bifurcated stent, and/or graft 204 can be a single bifurcated graft. In certain embodiments, stent 202 and/or graft 204 can be formed of multiple modular components. In FIG. 4B, on the other hand, an AAA stent-graft 210 includes three stents 212, 214, and 216, that are connected, and partially covered, by a graft 218. In some embodiments, at least one of the stents is entirely covered by the graft. Methods of making AAA stent-grafts are described, for example, in Goicoechea et al., U.S. Pat. No. 6,165,213.

The stent-graft can include one or more releasable therapeutic agents or pharmaceutically active compounds, such as described in Phan et al., U.S. Pat. No. 5,674,242; U.S. Ser. No. 10/232,265, filed on Aug. 30, 2002, and entitled "Drug Delivery Particle"; U.S. Published Application No. 2003/0003220 A1, published on Jan. 2, 2003; and U.S. Published Application No. 2003/0018380 A1, published on Jan. 23, 2003. In some embodiments, all of the components of the stent-graft (e.g., the stent and the graft) include a therapeutic agent or a pharmaceutically active compound. In other embodiments, one component includes a therapeutic agent or a pharmaceutically active compound, while another component does not. Examples of therapeutic agents and pharmaceutically active compounds include anti-thrombogenic agents, thrombogenic agents, antioxidants, anti-inflammatory agents, anesthetic agents, anti-coagulants, anti-restenosis agents, thrombosis agents, immunosuppressant agents, and antibiotics.

Alternatively or in addition, ceramic fiber 12 can include, or can be modified to include, the therapeutic agent, drug, or pharmaceutically active compound. For example, certain ceramics are relatively porous. The drug can be loaded on the ceramics by dipping or soaking the ceramics in a solution containing the drug, and allowing the drug to diffuse through the pores. In some cases, the drug can be loaded on the ceramics by applying the drug under pressure to infuse it into any pores. In certain embodiments, ceramic fiber 12 can be selectively surface modified to be relatively hydrophilic or hydrophobic. A drug can then be chemically bonded to the modified surface of the fiber. In some cases, ceramic fiber 12 can be roughened by, e.g., sand blasting, scraping or scoring the fiber. Ceramic fiber 12 can be pitted (by, e.g., laser or molding processes) or made porous (by, e.g., a chemical process). Ceramic fiber 12 can include a tie layer that can adhere a drug to the ceramic fiber. The ceramic fiber can be coated with, e.g., a polymer coating that contains a therapeutic agent.

In some cases, the ceramic fiber can include a charged coating that renders the ceramic fiber capable of carrying a charged therapeutic agent. Charged coatings are described, for example, in Palasis, U.S. Pat. No. 6,506,408 B1, which is hereby incorporated by reference. For example, a ceramic fiber can be positively charged, while a therapeutic agent can be negatively charged. The negatively charged therapeutic agent can be, e.g., a therapeutic agent that can associate with the positively charged moieties on the ceramic at below about a physiological pH (e.g., below about 7.4), and that can be substantially released therefrom at or above about a physiological pH. Negatively charged therapeutic agents include nucleic acids such DNA, cDNA, RNA, antisense DNA or RNA, nucleotides, proteins, and oligopeptides.

One or more negatively charged therapeutic agents can be associated with the ceramic fiber. Moreover, it is also possible for the ceramic fiber to be associated with one or more other therapeutic agents that are not negatively charged. Thus, the ceramic fiber, in addition to negatively charged therapeutic agents, can include, for example, cationically charged, amphoteric or neutral therapeutic agents. The therapeutic agents do not have to be released from the ceramic fiber upon contact with fluid or tissue having a physiological pH. A ceramic fiber can thus include one or more negatively charged therapeutic agents and one or more other therapeutic agents that are not necessarily ionically bound to the ceramic fiber.

Figure 5A:
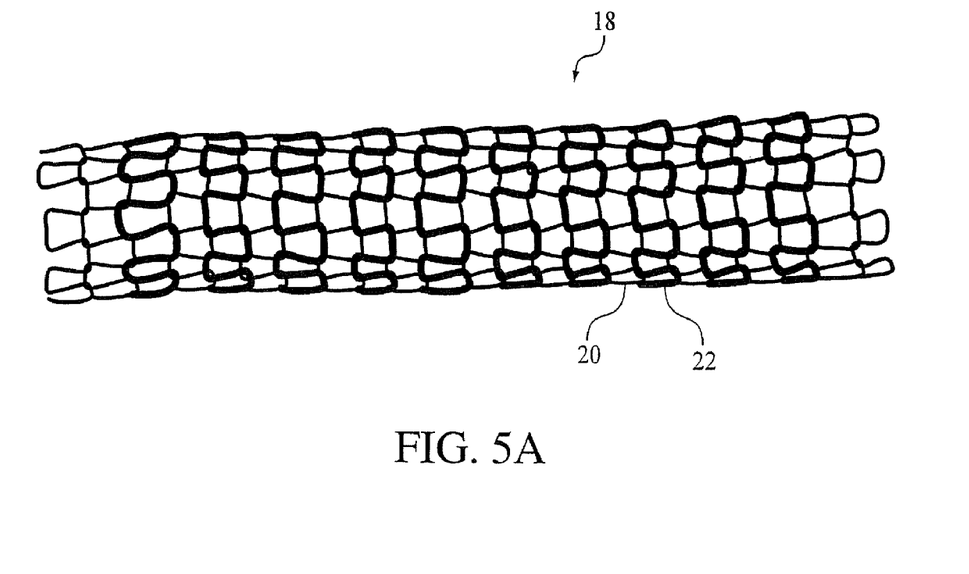
FIG. 5A is a perspective view of an endoprosthesis.
Figure 5B:
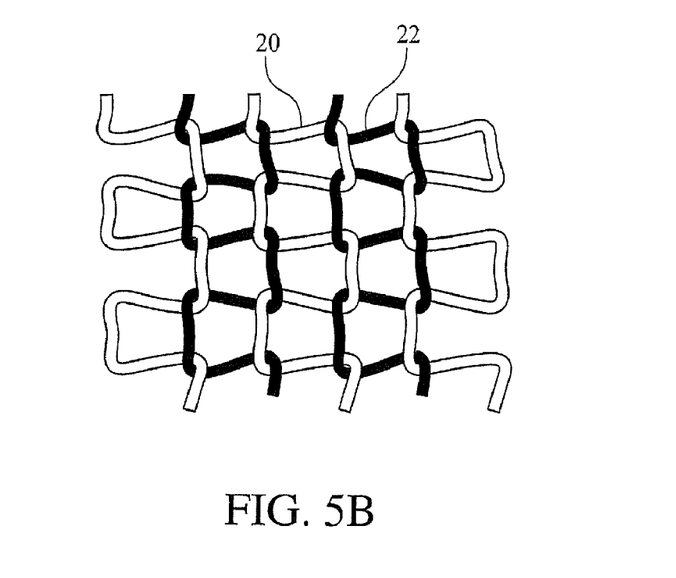
FIG. 5B is a detailed view of the endoprosthesis of FIG. 5A.

In some embodiments, an endoprosthesis includes more than one fiber. Referring to FIGS. 5A and 5B, a co-knitted stent 18 is shown including a ceramic fiber 20 and a non-ceramic fiber 22. Ceramic fiber 20 can generally be as described above for fiber 12. Non-ceramic fiber 22 can be a material selected for its strength and/or elasticity. Examples of materials for non-ceramic fiber 22 include, stainless steel (e.g., 300 series stainless steel), Nitinol (which can provide endoprosthesis 18 with superelasticity and shape memory properties), and composite materials as described in Heath, U.S. Pat. No. 5,725,570, and Mayer, U.S. Pat. No. 5,800,511. In some cases, non-ceramic fiber 22 can be a bioabsorbable polymer or a non-bioabsorbable polymer. In other embodiments, stent 18 can be formed of two different ceramic fibers, e.g., a silicon borocarbonitride fiber and an aluminum oxide fiber. The two ceramic fibers can be the same. Either, both, or neither of the fibers can include a therapeutic agent or drug, e.g., by dipping, spray coating, or pad printing.

Stent 18 can be formed by knitting or weaving fibers into a tubular member. For example, fibers 20 and 22 (or two different ceramic fibers) can be continuous knitted in an alternating, sequential co-knit fashion, resulting in successive alternating rows of different material in a single knit structure. Alternatively, a co-knit tubular structure can also be formed by, for example, using a parallel co-knitting process. Co-knitting processes are further described, for example, in Andersen, U.S. Pat. No. 5,366,504.

Figure 6A:
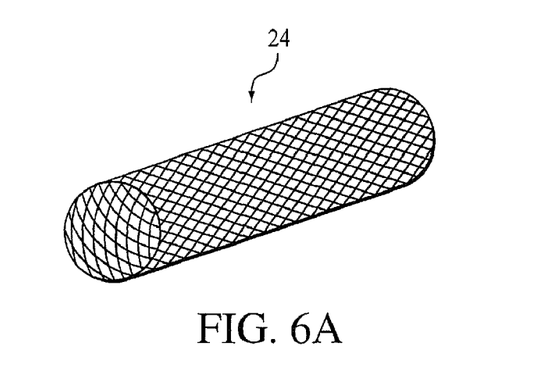
FIG. 6A is a perspective view of an endoprosthesis.
Figure 6B:
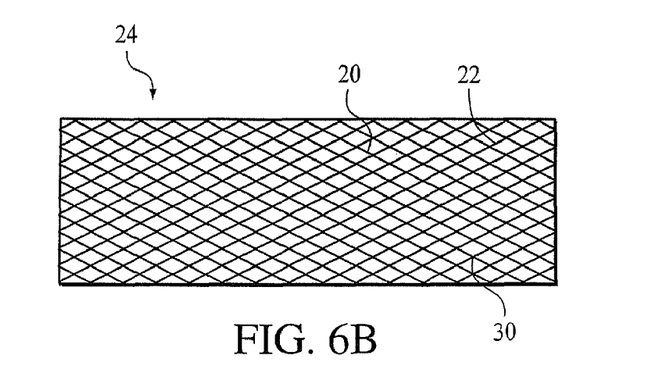
FIG. 6B is a detailed view of the endoprosthesis of FIG. 6A.

Referring to FIGS. 6A and 6B, in some embodiments fibers 20 and 22 (or two different ceramic fibers) can be co-woven to form a stent 24 of open mesh or weave construction, having two sets of oppositely directed, parallel and spaced apart helically woven fibers. Fibers 20 and 22 are interwoven in an over and under braided configuration, forming intersection points 30. Woven stents and methods of making them are described further in, for example, Mayer, U.S. Pat. No. 5,800, 511. In some embodiments, the stent can be formed of coils of fibers 20 and 22. In other embodiments, fibers 20 and 22 can be knotted, twisted, bent, or crocheted to form a stent.

The tubular structures described above having one or more ceramic fibers ("ceramic tubular structures") can be incorporated into a variety of medical devices. For example, the ceramic tubular structures can be attached (interiorly and/or exteriorly) to one or more graft materials, or be placed between multiple layers of graft material, to form a vascular graft. Examples of graft materials, such as polytetrafluoroethylene (PTFE) and expanded PTFE, and methods of making a graft are described in Lentz et al., U.S. Pat. No. 6,428,571. In some cases, the graft itself can be made of ceramic fibers. In some embodiments, the graft can include a therapeutic agent or pharmaceutically active compound.

The ceramic tubular structures can be attached (interiorly and/or exteriorly) to a polymer tube, or be placed between multiple layers of polymer tubes to form a composite tubing or a catheter. Suitable polymers are described, for example, in U.S. Published Application No. 2002/0165523 A1, published on Nov. 7, 2002. The composite tubing or catheter can include multiple polymer layers, as described in U.S. Published Application No. 2002/0165523 A1. Methods of making a reinforced catheter, e.g., having a braided layer, are described in, for example, Wilson et al., U.S. Pat. No. 6,425,898, which is hereby incorporated by reference. The ceramic tubular structures can be used in, for example, chronic infusion catheters, AV catheters, neurointerventional catheters, drainage catheters, or inflation/dilatation catheters. In some embodiments, ceramic fibers can be used to reinforce endoscopes and/or tubing (e.g., in embodiments in which torqueability, kink resistance, flexibility, and/or crush resistance are desired). Tubing for medical applications is described, for example, in Wendlandt et al., U.S. Published Application No. 2003/0176849, which is hereby incorporated by reference.

The composite tubing can be drawn and blow molded to form a medical balloon, e.g., one having ceramic structure between two polymer layers. Methods of forming a medical balloon, including suitable materials, are described, for example, in U.S. Ser. No. 10/263,225, filed on Oct. 2, 2002, and entitled "Medical Balloon". The ceramic tubular structures, which can be knitted, woven, braided, co-knitted, or co-woven, can reinforce the medical devices. A medical device can have two or more ceramic tubular structures.

Figure 7:
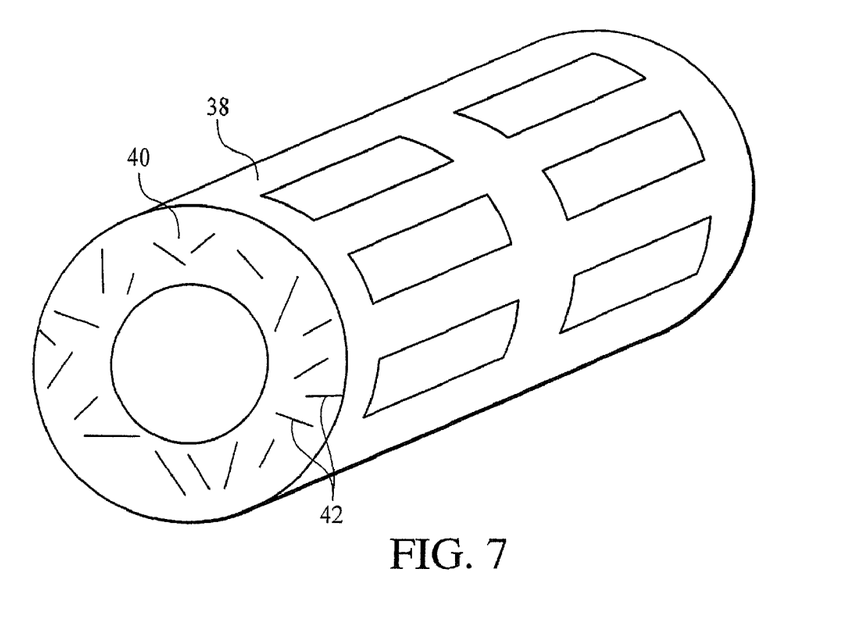
FIG. 7 is a cross-sectional view of an endoprosthesis.

In still other embodiments, relatively small segments of ceramic fiber 12 are used to form a medical device. Referring to FIG. 7, an endoprosthesis 38 (as shown, a stent) includes a polymer matrix 40 containing chopped ceramic fibers 42 embedded in the matrix. Chopped ceramic fibers 42 embedded in polymer matrix 40 can enhance the strength and/or biocompatibility of the medical device. In some embodiments, chopped fibers 42 can include a therapeutic agent or pharmaceutically active compound. Fibers 42 can be formed by chopping ceramic fibers 12 into smaller pieces.

Although ceramic fibers 42 are shown in a stent in FIG. 7, ceramic fibers 42 can be used in any of a number of different medical devices. For example, ceramic fibers 42 can be used to reinforce a suture. A suture that is reinforced with ceramic fibers 42 can then be used to weave, knit, or otherwise form a graft or covering. In some cases, ceramic fibers 42 can be used to reinforce a stent-graft, polymer covering, or graft. A graft that is reinforced with ceramic fibers 42 may be able to support itself without requiring the support of a stent. Ceramic fibers 42 can be dispersed relatively evenly throughout the graft, or can be dispersed asymmetrically. For example, the graft can include a higher density of ceramic fibers at the ends of the graft. In such cases, the ceramic fibers may impart the ends of the graft with enhanced stiffness, such that the graft may be able to stay open without the support of a stent.

The grafts or stent-grafts can include synthetic vascular grafts that can be used for replacement of blood vessels in part or in whole. The grafts can be tubular and can have, e.g., a woven, knit or velour construction. Preferred materials for the grafts and covering materials for the stent-grafts include polyethylene terephthalate and polytetrafluoroethylene. The vascular grafts can be reinforced with, for example, helices, and/or rings (e.g., to help provide uniform strength over the entire surface of the graft tubing). The materials of which such grafts can be constructed are biologically compatible materials including, but not limited to, thermoplastic materials such as polyester, polytetrafluoroethylene (PTFE), silicone and polyurethanes. The preferred materials include polyester fibers and PTFE. In some cases, the graft can have a coating that includes a polymeric material and one or more therapeutic agents and/or pharmaceutically active compounds (e.g., paclitaxel, sirolimus, everolimus). The polymeric material can be a copolymer of polycaprolactone and polylactic acid. Grafts are described in Schmitt, U.S. Pat. No. 5,509,931; Schmitt, U.S. Pat. No. 5,527,353; and Popadiuk et al., U.S. Pat. No. 5,556,426, all of which are hereby incorporated by reference.

Ceramic fibers 42 can be used to reinforce a balloon. An advantage to a balloon reinforced by ceramic fibers 42 is that the balloon can have a relatively low wall thickness (e.g., about 0.001 inch), while simultaneously being strong.

Fibers 42 are generally elongate structures having lengths greater than widths or diameters. In some cases, fibers 42 can have a length of from about five microns to about 25,000 microns (e.g., from about ten microns to about 1,000 microns, from about ten microns to about 100 microns). Fibers 42 can have a length equal to or greater than about five microns (e.g., greater than about 5000 microns; greater than about 10,000 microns; greater than about 15,000 microns; greater than about 20,000 microns), and/or equal to or less than about 25,000 microns (e.g., less than about 20,000 microns; less than about 15,000 microns; less than about 10,000 microns; less than about 5,000 microns). The lengths of fibers 42 may be uniform or relatively random.

Fibers 42 can have a width or diameter of from about one micron to about 50 microns (e.g., about ten microns). Fibers 42 can have a width or diameter that is equal to or greater than about one micron (e.g., greater than about five microns, greater than about ten microns, greater than about 15 microns, greater than about 20 microns, greater than about 25 microns, greater than about 30 microns, greater than about 35 microns, greater than about 40 microns, greater than about 45 microns), and/or equal to or less than about 50 microns (e.g., less than about 45 microns, less than about 40 microns, less than about 35 microns, less than about 30 microns, less than about 25 microns, less than about 20 microns, less than about 15 microns, less than about ten microns, less than about five microns). The width or diameter can be uniform or relatively random.

In some cases, such as when fibers 42 are used to reinforce balloons, fibers 42 can have a width or diameter of less than about three microns (e.g., less than about two microns). In certain embodiments, fibers 42 can have a width or diameter of from about two nanometers to about four nanometers.

In some embodiments, fibers 42 have length to width aspect ratios of from about 5:1 to about 500:1 (e.g., from about 5:1 to about 20:1), although higher aspect ratios are possible. Fibers 42 can have a length to width aspect ratio equal to or greater than about 5:1 (e.g., greater than about 50:1, greater than about 100:1, greater than about 150:1, greater than about 200:1, greater than about 250:1, greater than about 300:1, greater than about 350:1, greater than about 400:1, greater than about 450:1), and/or equal to or less than about 500:1 (e.g., less than about 450:1, less than about 400:1, less than about 350:1, less than about 300:1, less than about 250:1, less than about 200:1, less than about 150:1, less than about 100:1, less than about 50:1).

The width used to determine the aspect ratio can be the narrowest or broadest width. The length can be the largest dimension of a fiber. Mixtures of fibers having two or more different aspect ratios and/or dimensions can be used.

Smaller ceramic fibers 42 may be used to reinforce thinner walls of an endoprosthesis, while larger ceramic fibers 42 may be used to reinforce thicker walls of an endoprosthesis. Preferably, smaller fibers are used to reinforce, for example, sutures or balloons, which may require smaller fibers because of their smaller size. In some cases, the fibers can strengthen the device being reinforced such that the device can have even thinner walls. Larger fibers, on the other hand, preferably are used to reinforce a catheter shaft or a stent covering.

Ceramic fibers 42 can be placed in different sections of an endoprosthesis (such as a catheter) to provide, e.g., variable stiffness. For example, a catheter can have a higher concentration of ceramic fibers 42 in its proximal end than in its distal end. Thus, the proximal end may have enhanced stiffness, which can increase the pushability, torque, kink resistance, and/or control of the catheter. If the distal end has a lower concentration of ceramic fibers 42, then it can serve as an atraumatic tip and provide flexibility when, for example, the catheter is negotiating a tortuous lumen.

Ceramic fibers 42 can be axially, radially, and/or circumferentially oriented in a medical device or component. The orientation of ceramic fibers 42 in a medical device or component can be selected to form a pattern or can be random. In certain embodiments, the orientation of ceramic fibers 42 in a medical device or component can be selected to enhance reinforcement of the device or component, and/or can be selected to enhance the flexibility, radial strength, and/or torqueability of the device or component.

Ceramic fibers 42 can have a variety of configurations or shapes. Fibers 42 can have a cross-section that is circular or non-circular, such as oval, or regularly or irregularly polygonal having three, four, five, six, seven, or eight or more sides. In some cases, fibers 42 can be flat. Fibers 42 can be in the shape of a ribbon (e.g., a flat or wavy ribbon). Along their length, fibers 42 can be, for example, straight, wavy, coiled, or folded. Fibers 42 can be textured, e.g. to combine more easily with the matrix in which they are suspended and/or to hold therapeutic agents for delivery. The surfaces of fibers 42 can be roughened. As an example, fibers 42 can be porous, etched, or grooved. Fibers 42 can have a uniform or non-uniform thickness, e.g., the fibers can taper along their lengths. Mixtures of fibers having two or more different configurations or shapes can be used. In other embodiments, thin, flat shard-like fibers having irregular shapes can be used. Fibers 42 can be, e.g., whiskers, such as those described in Javier Llorca, "Fatigue of Particle- and Whisker-Reinforced Metal-Matrix Composites," *Progress in Materials Science* 47 (2002), 283-353, which is hereby incorporated by reference.

Polymer matrix 40 can include one or more polymers that are biocompatible. For example, for vascular stents or stent-grafts, the polymer preferably has acceptable vascular compatibility, e.g., relatively low thrombogenecity and low cytotoxicity. For non-vascular stents or stent-grafts, the polymer is preferably stable in various bodily fluids. Suitable polymers are described in U.S. Ser. No. 10/229,548, filed on Aug. 28, 2002, and entitled "Medical Devices and Methods of Making the Same".

Polymer matrix 40 and ceramic fibers 42 can be mixed together and formed into a medical device, e.g., by extruding the polymer matrix and the ceramic fibers 42. For example, methods of making a tube or a catheter from a composite including a polymer are described in Weber, U.S. Published Application No. 2003/0065355, which is hereby incorporated by reference. The tube can be formed into a medical balloon, as described in U.S. Ser. No. 10/263,225, filed on Oct. 2, 2002, and entitled "Medical Balloon". Methods of making a stent, including methods of preferentially orienting fibers, are described in, for example, U.S. Ser. No. 10/229,548, filed on Aug. 28, 2002, and entitled "Medical Devices and Methods of Making the Same". Methods of making a vascular graft are described in, for example, Lentz et al., U.S. Pat. No. 6,428,571. The mixture of polymer matrix 40 and fibers 42 can be used to make an embolic filter, e.g., a filter membrane, as described in, for example, Weber, U.S. Published Application No. 2003/0065355, incorporated above.

In some cases, the mixture of polymer matrix 40 and fibers 42 can be injection molded to form certain medical devices. For example, a mixture containing a relatively hard polymer, e.g., polycarbonate or acrylonitrile-butadiene-styrene (ABS), and fibers 42 can be injection molded to form a port housing, as described, e.g., in U.S. Ser. No. 10/117,947, filed Apr. 8, 2002, and entitled "Medical Devices".

In certain embodiments, medical devices can be reinforced with beads (with or without fibers 42). The beads can be spherical, oval, or elliptical. The beads can have widths that are equal to the diameters of the beads.

The mixture of polymer matrix 40 and fibers 42 can contain a radiopaque material, a material that is visible by magnetic resonance imaging (MRI), and/or an ultrasound contrast agent. Examples of radiopaque materials include tantalum, tungsten, platinum, palladium, or gold. The radiopaque material can be placed inside an inclusion member. Alternatively or in addition, the radiopaque material, e.g., a band of radiopaque material, can be placed on a medical device at selected positions, such as, for example, on a catheter adjacent to a balloon. In some cases, fibers 42 can be rendered radiopaque (for example, by incorporating (e.g., coating) radiopaque metals or agents into the fibers).

Examples of MRI visible materials include non-ferrous metal-alloys containing paramagnetic elements (e.g., dysprosium or gadolinium) such as terbium-dysprosium, dysprosium, and gadolinium; non-ferrous metallic bands coated with an oxide or a carbide layer of dysprosium or gadolinium (e.g., $Dy_2O_3$ or $Gd_2O_3$); non-ferrous metals (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; and nanocrystalline particles of the transition metal oxides (e.g., oxides of Fe, Co, Ni).

The ultrasound contrast agent can be any material that enhances visibility during ultrasound imaging. An ultrasound contrast agent can include a suspension having trapped bubbles of sufficient size to deflect sound waves. In some cases, ceramic fibers 42 can be rendered visible to ultrasound spectroscopy by, for example, surface roughening, bubble inclusions, and/or a coating. Any of the medical devices described above can include an MRI contrast agent, a radiopaque material, and/or an ultrasound contrast agent, in any combination or arrangement.

Ceramic fibers 42 can be used to form a composite. Composites are described in "Fatigue of Particle- and Whisker-Reinforced Metal-Matrix Composites," incorporated above, and in references described therein. While ceramic fibers 42 are embedded in polymer matrix 40 in FIG. 4, in some cases ceramic fibers 42 can be embedded in a metal (e.g., stainless steel, titanium, iridium), to form a ceramic reinforced metal matrix composite. The metal can then be used to make a medical device (e.g., a stent).

In certain embodiments, a ceramic fiber can be formed by depositing ceramic material onto a substrate (e.g., a metal wire filament, as described in, for example, Heath, U.S. Pat. No. 5,725,570, and Mayer, U.S. Pat. No. 5,800,511). The ceramic can be deposited using techniques such as physical vapor deposition (PVD), chemical vapor deposition (CVD), or metalorganic chemical vapor deposition (MOCVD).

OTHER EMBODIMENTS

Ceramic fibers 12 and 42 as described above can be used in many types of medical devices. Examples of such medical devices include catheters, guidewires, balloons, filters (e.g., vena cava filters), stents, stent-grafts, vascular grafts, intraluminal paving systems, and implants. Such devices can be implanted or otherwise utilized in body lumina and organs such as the coronary vasculature, esophagus, trachea, colon, biliary tract, urinary tract, prostate, and brain.

The filters can include, for example, thrombus filters that can be placed at a selected location within the vascular system (e.g., the vena cava) and removed when no longer required. In some embodiments, an implanted vascular filter can have a polymeric material/drug outer coating thereon. For example, the filter can have a polymeric material/paclitaxel outer coating (e.g., a polylactic acid/polycaprolactone copolymer/paclitaxel coating). The polymeric coating can also have incorporated therein or thereon any other therapeutic agent that is used for reducing the formation of, or complications due to, clot formation or neointima formation. Such agents include antithrombogenic agents and thrombolytic agents and other antiproliferative agents. Filters are described in International Application No. WO 96/17634 and International Application No. WO 96/12448, which are hereby incorporated by reference.

In some embodiments, a polymer matrix including chopped fibers can be used as an intraluminal paving system. In such intraluminal paving systems, the polymer matrix can be applied directly to an interior surface of vascular or non-vascular lumina. An intraluminal paving system can be formed, for example, by admixing a drug agent with a liquid polymer, in the absence of a solvent, to form a liquid polymer/drug agent mixture. The mixture can then be applied directly to a luminal surface by any conventional method, such as by injecting the mixture against the luminal surface. Curing of the mixture can occur in-situ. To facilitate curing, a cross-linking or curing agent can be added to the mixture prior to application thereof to the luminal surface. Curing can also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In some cases, the drug agent in the intraluminal paving system is paclitaxel. The paclitaxel can be incorporated in the polymeric material alone or in combination with another drug agent. The polymeric material incorporating the paclitaxel and, if desired, any additional therapeutic agent(s), can be either bioabsorbable or biostable. Any of the polymers described herein that may be formulated as a liquid may be used to form the polymer/drug agent mixture for use as an intraluminal paving system.

In certain embodiments, ceramic fibers 12 and/or 42 can be used in aneurysm filling devices (e.g., brain aneurysm filling devices). In such embodiments, the ceramic fibers can be radiopaque and/or MRI-compatible. The ceramic fibers can be used to form the aneurysm filling devices (e.g., an aneurysm filling device can be formed by a continuous ceramic fiber) and/or as reinforcement in the aneurysm filling devices. In some embodiments, the fibers can be combined (e.g., woven, braided) with another type of material. An aneurysm filling device that includes one or more ceramic fibers can also include one or more agents (e.g., thrombotic agents). Aneurysm filling devices are described, for example, in Bashiri et al., U.S. Pat. No. 6,468,266; Abrams, U.S. Pat. No. 6,331,184; Wallace et al., U.S. Pat. No. 6,280,457; Palermo et al., U.S. Pat. No. 6,190,373; Bashiri et al., U.S. Pat. No. 6,165,178; and Chin et al., U.S. Pat. No. 5,928,260.

All publications, applications, references, patents referred to above are incorporated by reference in their entirety.

Other embodiments are within the following claims.

What is claimed is:

1. A medical device, comprising:
a structure comprising a polymer matrix and a first ceramic fiber embedded in the matrix, the first ceramic fiber comprising a first metalloid, wherein each dimension of the first ceramic fiber is equal to or greater than one micron, and the device is in the form of a stent or a stent-graft.

2. The device of claim 1, wherein the first ceramic fiber further comprises a second metalloid.

3. The device of claim 2, wherein the first metalloid comprises an element selected from the group consisting of silicon and boron.

4. The device of claim 2, wherein the first ceramic fiber comprises silicon borocarbonitride.

5. The device of claim 1, wherein the first ceramic fiber further comprises a non-metallic element.

6. The device of claim 1, wherein the first ceramic fiber is at least about five microns long.

7. The device of claim 1, wherein the first ceramic fiber is from about five microns to about 25,000 microns long.

8. The device of claim 1, wherein the first ceramic fiber is at least about five microns wide.

9. The device of claim 1, wherein the first ceramic fiber is from about five microns to about 500 microns wide.

10. The device of claim 1, wherein the first ceramic fiber extends continuously along an entire length of the device.

11. The device of claim 1, further comprising a second ceramic fiber different from the first ceramic fiber.

12. The device of claim 1, wherein the structure is a tubular member.

13. The device of claim 1, in the form of a stent.

14. The device of claim 1, in the form of a stent-graft.

15. The device of claim 1, wherein the first ceramic fiber extends continuously along an entire length of the device.

16. A medical device, comprising:
a structure comprising a polymer matrix and a first ceramic fiber embedded in the matrix, the first ceramic fiber comprising a first metalloid, wherein each dimension of the first ceramic fiber is equal to or greater than one micron, and the device is in the form of a stent, a stent-graft, a graft, a medical balloon, or a catheter, wherein the device further comprises a therapeutic agent.

17. A medical device, comprising:
a structure comprising a polymer matrix and a first ceramic fiber embedded in the matrix, the first ceramic fiber comprising a first metalloid, wherein each dimension of the first ceramic fiber is equal to or greater than one micron, and the device is in the form of a stent, a stent-graft, a graft, a medical balloon, or a catheter, wherein the first ceramic fiber extends helically about the device.

* * * * *